US00PP08191P

United States Patent [19]

Hetherington

[11] Patent Number: Plant 8,191

[45] Date of Patent: Mar. 30, 1993

[54] ORCHID 'PINK DAWN'

[75] Inventor: Ernest E. Hetherington, Arcadia, Calif.

[73] Assignee: Stewart Orchids, Carpenteria, Calif.

[21] Appl. No.: 682,133

[22] Filed: Apr. 8, 1991

[51] Int. Cl.[5] ..... A01H 5/00
[52] U.S. Cl. ..... Plt./87.3
[58] Field of Search ..... Plt./68, 87.3

*Primary Examiner*—James R. Feyrer
*Attorney, Agent, or Firm*—Howard A. Kenyon

[57] ABSTRACT

A new and distinct variety of orchid, more particularly a Cymbidium hydrid cultivar plant having flowers of large size and clear color with flowers erectly carried and well spaced on strong sprays. The new variety is distinct from siblings of its grex by its outstanding vigorous growth habit as well as frequency and freedom of bloom. Of primary note with this cultivar is its great vigor, compact growth habit and freedom of bloom and season which makes it extremely useful as a producer of Cymbidium flowers for the florist market.

1 Drawing Sheet

DISCOVERY OF THE NEW CULTIVAR

The orchid of this application was discovered by the undersigned as an outstanding member of a large sibling population of the hybrid orchid Cymbidium Bangkok Beauty. (Herein abbreviated as Cym. Bangkok Beauty). In April 1972 Cym. Bangkok Beauty had been developed in the Orchid Nursery of Fred A. Stewart Inc. at San Gabriel, Calif. by crossing Cym. Paracel 'Picture' AM/AOS×Cym. Marquesa Prescott 'Braemar'. The Paracel 'Picture' parent was the pod parent (mother plant). The resultant grex was registered by the Stewart Nursery with the orchid hybrid registration committee in London, England in 1977 and published in the 1976–1980 volume of Sanders Orchid Hybrid List. The new orchid was registered under Stewart Cross number 2,340 Cym. Bangkok Beauty. In March of 1984 the new cultivar appeared as a single outstanding plant among a large population of siblings of Bangkok Beauty, all cultivated and blooming at Stewarts Santa Barbara Nursery. The plant of the new cultivar was immediately recognizable as superior in its flowering and general growth habit to all other members of large population of the hybrid group Bangkok Beauty. After the new variety had been observed for a period of time its other features of superior growth and structure were also noted.

ASEXUAL REPRODUCTION

After its discovery in March 1984 the original plant was placed in the laboratories of Armroy Stewart Inc. Nursery. During the years since 1984 a large number of plants of the new cultivar have been asexually produced by the meristem tissue culture process. Portions of tissue called meristems, comprised of unspecialized cells, capable of later differentiation were cut from the plant and developed, under carefully controlled sterile conditions into new individual plants. This has been an ongoing process to cultivar this exceptional cultivar. The population thus produced has been carried under the code number of B118, B8522 and B8811. All of these populations have been asexually propagated tissue from this cultivar.

All of the propagations reproduced true to the original in both plant, flower and other characteristics. A substantial cross section have flowered. They are exactly the same as the mother clone, with no signs of mutation. All plants in the variety have continued to be readily distinguishable from both parents and all other siblings of Bangkok Beauty in flower quality, plant growth habit and other characteristics. The new cultivar have been designated as Cym. Bangkok Beauty 'Pink Dawn'.

DESCRIPTION OF THE PHOTOGRAPHS

The upper photograph is a closeup view of a spray of flowers typical of the new variety.

The lower photograph shows the same flowers but is viewed from a greater distance to reveal the appearance of the flower spray and its relationship to the compact general growth habit of the plant.

DESCRIPTION OF THE PLANT

The plant with its flowers is illustrated in the color photograph accompanying this specification. In some respects, the plant is typical of a Cymbidium hybrid, however, because of its compact growth habit, with many flowering growths and short leaves erectly carried it is outstanding in these characteristics. The leaves average approximately 50–60 centimeters in length and average 4–5 centimeters in width. The plant attains a growth height of about 70 centimeters. When measured from base of the plant top of the leaves. The flower sprays generally extend above the foliage to a total height of about 90 cm. An outstanding characteristic of the plant in addition to its compactness is the relatively small pseudobulb size which is important in commercial cut flower production of Cymbidiums. The bulbs average 11.2 cm high and 13.0 cm in circumference. The strong flower sprays are borne from the base of the growths which develop in the current season and are of superior strength and erect carriage. The plants are exceptionally hardy in comparison with many other Cymbidiums and have been virus and pathogen free during development both in the original plant of Bangkok Beauty 'Pink Dawn' and in the meristem population of this cultivar.

DESCRIPTION OF THE FLOWERS

The outstanding merit of the new variety in addition to vigor and dependability of bloom is the size, clarity and delicacy of coloring of the flowers. The pastel colorations are in harmony with the spottings and markings of the large lips. What is especially notable is the excellent carriage of the very large flowers with each flower in perfect position on the long stem and the very high flower count to a stem. This is a characteristic not always found in Cymbidiums. The sepals and petals are delicate clear pink. The color values to follow are taken from The *R.H.S Color Chart* in association with the flower council of Holland. From a distance, sepals and petals appear to be a delicate clear pink best described as a medium rose pink, of near Fan #1, sheet #55 in the red group, swatches A and B. However, with close examination, subtle deeper pink and lighter, near white, striations or bands are expressed in sepals as well as petals. Such striations generally follows the lines of venation; vein coloration being of noticably darker pink shadings. The top sepal central portion is distinctly and conspicuously a deeper pink, bounded by marginal strips of lighter pink shades, and forms a distinct, pointed uniformly lapping the exterior surface on each side of the top sepal centerline. The flowers hold their color very well over a period of three to five weeks from the opening of the basal flowers to the opening of the terminal flowers on the stout by gently curving vertically ascending spike.

The mildly protruding tip of the column is white in crisp contrast to the gently curved, pink shaded, top surface portion of the column, and takes on the appearance of a single white eye.

The flowers of this cultivar are larger and stronger in structure than the average grex or sibling of this hybrid. The flowers average 10 to 12 centimeters in width with a petal width of 4–5 centimeters. This new cultivar carries from 12 to 17 flower well spaced on the spray on a mature plant. What is especially notable is the flowers are perfectly carried on strong erect flower spikes, but not on too long a flower spike. The petals are flat substantially smooth and slightly cupped and well carried in contrast to other cultivars of this grex and lines of breeding. The pedicels of the flowers are long enough for each flower to be well spaced on the stem. The sepals and petals are in symetrical balance to the lip and create a good round shape to the flower as a whole. What is exceptional in this particular cultivar is the flowers last well regardless of weather conditions or temperature. They last for six to eight weeks on the plant if uncut. The blooming season is primarily winter into spring, which can vary according to cultural conditions where it is grown. What has been observed in this culivar unlike many other Cymbidiums initiates a succession of flower spikes which gives longer season of bloom. A 10 bulb mature plant produces 4 to 6 flower spikes in an average flowering season.

The above described characteristics of the new variety make it of exceptional value in a commercial Cymbidium cut flower market as well as for plant sales.

The exceptional vigor of this particular cultivar, excellent blooming season, total reliability of bloom and freedom of bloom are characteristics which set this particular cultivar above not only siblings in the grex but other gregi in this entire line of breeding or other lines of cymbidium breeding.

What is claimed is:

1. A new and distinct variety in the hybrid genus Cymbidium substantially as described and illustrated herein which was discovered as a superior variety in the grex Cymbidium 'Bangkok Beauty' named 'Pink Dawn' characterized by a combination of clearness of coloring, superior flower substance, size, shape and further characterized by its exceptional vigor, reliability of bloom and lasting qualities.

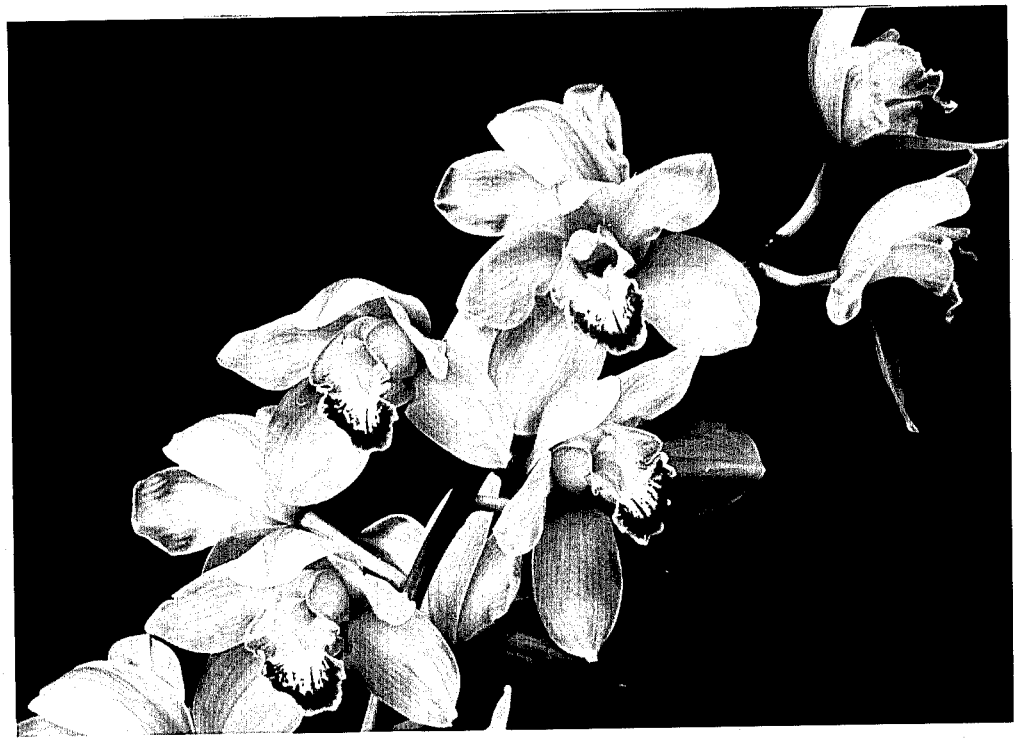
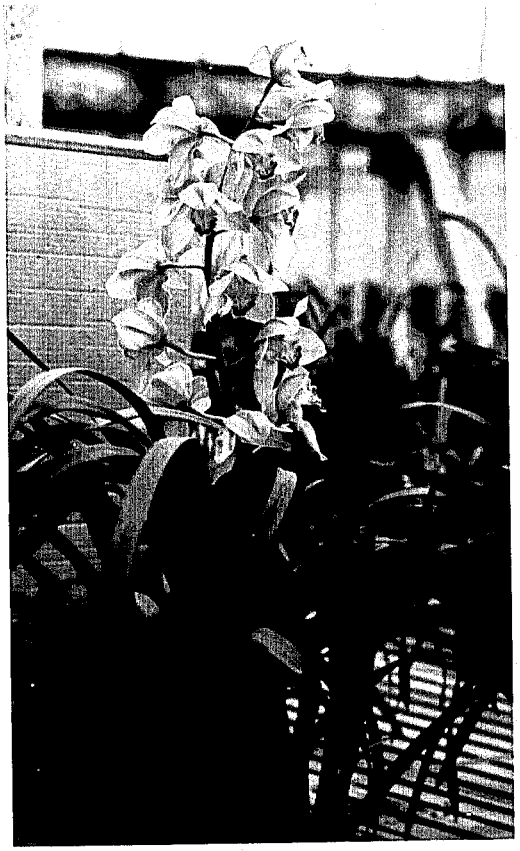

* * * * *